(12) United States Patent
Goodman

(10) Patent No.: US 10,660,694 B2
(45) Date of Patent: May 26, 2020

(54) VESSEL SEALING INSTRUMENT AND SWITCH ASSEMBLIES THEREOF

(71) Applicant: COVIDIEN LP, Mansfield, MA (US)

(72) Inventor: Kelley D. Goodman, Erie, CO (US)

(73) Assignee: Covidien LP, Mansfield, MA (US)

( * ) Notice: Subject to any disclaimer, the term of this patent is extended or adjusted under 35 U.S.C. 154(b) by 928 days.

(21) Appl. No.: 14/800,070

(22) Filed: Jul. 15, 2015

(65) Prior Publication Data

US 2016/0058498 A1  Mar. 3, 2016

Related U.S. Application Data

(60) Provisional application No. 62/042,543, filed on Aug. 27, 2014.

(51) Int. Cl.
*A61B 18/14* (2006.01)
*A61B 18/00* (2006.01)

(52) U.S. Cl.
CPC .. *A61B 18/1442* (2013.01); *A61B 2018/0063* (2013.01); *A61B 2018/00607* (2013.01);
(Continued)

(58) Field of Classification Search
CPC ............ H01H 13/7057; A61B 17/2841; A61B 2018/00922; A61B 2018/00958
See application file for complete search history.

(56) References Cited

U.S. PATENT DOCUMENTS 2,176,479 A   10/1939 Willis
3,100,489 A   8/1963 Bagley
(Continued)

FOREIGN PATENT DOCUMENTS

CN   201299462       9/2009
DE   2415263 A1    10/1975
(Continued)

OTHER PUBLICATIONS

U.S. Appl. No. 09/591,328, dated Jun. 9, 2000 (Thomas Patrick Ryan).
(Continued)

*Primary Examiner* — Linda C Dvorak
*Assistant Examiner* — Ryan T Clark
(74) *Attorney, Agent, or Firm* — Carter, DeLuca & Farrell LLP

(57) ABSTRACT

A switch assembly for an electrosurgical instrument includes a switch housing, a switch, a first biasing member, and an additional biasing member. The switch is disposed within the switch housing and movably disposed between an activated position to initiate delivery of electrosurgical energy and a deactivated position to terminate delivery of electrosurgical energy. The first biasing member is selectively positionable adjacent the switch and in communication therewith. The first biasing member includes a first thickness that provides a first resistance to resist movement of the switch between the activated and the deactivated positions when positioned in the switch housing. The additional biasing member is selectively interchangeable with the first biasing member. The additional biasing member includes a different thickness that provides a different resistance to resist movement of the switch between the activated and the deactivated positions when positioned in the switch housing.

20 Claims, 4 Drawing Sheets

(52) U.S. Cl.
CPC ............... *A61B 2018/00922* (2013.01); *A61B 2018/00958* (2013.01)

(56) References Cited

U.S. PATENT DOCUMENTS

| | | | |
|---|---|---|---|
| 3,824,363 A * | 7/1974 | Fuller | G05G 1/105 |
| | | | 200/345 |
| 4,005,714 A | 2/1977 | Hiltebrandt | |
| 4,031,898 A | 6/1977 | Hiltebrandt et al. | |
| D249,549 S | 9/1978 | Pike | |
| D263,020 S | 2/1982 | Rau, III | |
| 4,370,980 A | 2/1983 | Lottick | |
| 4,461,297 A | 7/1984 | Sutter | |
| 4,461,305 A | 7/1984 | Cibley | |
| 4,552,143 A | 11/1985 | Lottick | |
| D295,893 S | 5/1988 | Sharkany et al. | |
| D295,894 S | 5/1988 | Sharkany et al. | |
| D298,353 S | 11/1988 | Manno | |
| D299,413 S | 1/1989 | DeCarolis | |
| 5,026,370 A | 6/1991 | Lottick | |
| 5,116,332 A | 5/1992 | Lottick | |
| 5,122,139 A | 6/1992 | Sutter | |
| 5,211,655 A | 5/1993 | Hasson | |
| D343,453 S | 1/1994 | Noda | |
| 5,290,287 A | 3/1994 | Boebel et al. | |
| 5,312,433 A | 5/1994 | Boebel et al. | |
| D348,930 S | 7/1994 | Olson | |
| D349,341 S | 8/1994 | Lichtman et al. | |
| 5,346,459 A * | 9/1994 | Allen | A61B 17/3496 |
| | | | 604/164.11 |
| 5,354,291 A * | 10/1994 | Bales | A61M 1/0064 |
| | | | 604/22 |
| D354,564 S | 1/1995 | Medema | |
| 5,383,875 A | 1/1995 | Bays et al. | |
| D358,887 S | 5/1995 | Feinberg | |
| 5,443,463 A | 8/1995 | Stern et al. | |
| 5,454,827 A | 10/1995 | Aust et al. | |
| 5,484,436 A | 1/1996 | Eggers et al. | |
| 5,498,256 A * | 3/1996 | Furnish | A61B 17/2909 |
| | | | 606/1 |
| 5,512,721 A | 4/1996 | Young et al. | |
| 5,601,601 A | 2/1997 | Tal et al. | |
| D384,413 S | 9/1997 | Zlock et al. | |
| 5,746,739 A | 5/1998 | Sutter | |
| H1745 H | 8/1998 | Paraschac | |
| 5,827,274 A | 10/1998 | Bonnet et al. | |
| D402,028 S | 12/1998 | Grimm et al. | |
| D408,018 S | 4/1999 | McNaughton | |
| 5,891,140 A | 4/1999 | Ginn et al. | |
| 5,891,142 A | 4/1999 | Eggers et al. | |
| 5,951,549 A | 9/1999 | Richardson et al. | |
| D416,089 S | 11/1999 | Barton et al. | |
| 6,010,516 A | 1/2000 | Hulka | |
| D424,694 S | 5/2000 | Tetzlaff et al. | |
| D425,201 S | 5/2000 | Tetzlaff et al. | |
| 6,106,542 A | 8/2000 | Toybin et al. | |
| 6,117,158 A | 9/2000 | Measamer et al. | |
| H1904 H | 10/2000 | Yates et al. | |
| D449,886 S | 10/2001 | Tetzlaff et al. | |
| D453,923 S | 2/2002 | Olson | |
| D454,951 S | 3/2002 | Bon | |
| D457,958 S | 5/2002 | Dycus et al. | |
| D457,959 S | 5/2002 | Tetzlaff et al. | |
| H2037 H | 7/2002 | Yates et al. | |
| D465,281 S | 11/2002 | Lang | |
| D466,209 S | 11/2002 | Bon | |
| D493,888 S | 8/2004 | Reschke | |
| D496,997 S | 10/2004 | Dycus et al. | |
| D499,181 S | 11/2004 | Dycus et al. | |
| D502,994 S | 3/2005 | Blake, III | |
| D509,297 S | 9/2005 | Wells | |
| D525,361 S | 7/2006 | Hushka | |
| 7,083,613 B2 | 8/2006 | Treat | |
| D531,311 S | 10/2006 | Guerra et al. | |
| D533,274 S | 12/2006 | Visconti et al. | |
| D533,942 S | 12/2006 | Kerr et al. | |
| D535,027 S | 1/2007 | James et al. | |
| 7,166,106 B2 | 1/2007 | Bartel et al. | |
| D538,932 S | 3/2007 | Malik | |
| D541,418 S | 4/2007 | Schechter et al. | |
| D541,611 S | 5/2007 | Aglassinger | |
| D541,938 S | 5/2007 | Kerr et al. | |
| 7,211,079 B2 | 5/2007 | Treat | |
| D545,432 S | 6/2007 | Watanabe | |
| D547,154 S | 7/2007 | Lee | |
| D564,662 S | 3/2008 | Moses et al. | |
| D567,943 S | 4/2008 | Moses et al. | |
| D575,395 S | 8/2008 | Hushka | |
| D575,401 S | 8/2008 | Hixson et al. | |
| D582,038 S | 12/2008 | Swoyer et al. | |
| 7,628,791 B2 | 12/2009 | Garrison et al. | |
| D617,900 S | 6/2010 | Kingsley et al. | |
| D617,901 S | 6/2010 | Unger et al. | |
| D617,902 S | 6/2010 | Twomey et al. | |
| D617,903 S | 6/2010 | Unger et al. | |
| D618,798 S | 6/2010 | Olson et al. | |
| D621,503 S | 8/2010 | Otten et al. | |
| D627,462 S | 11/2010 | Kingsley | |
| D628,289 S | 11/2010 | Romero | |
| D628,290 S | 11/2010 | Romero | |
| D630,324 S | 1/2011 | Reschke | |
| 7,922,718 B2 | 4/2011 | Moses et al. | |
| D649,249 S | 11/2011 | Guerra | |
| D649,643 S | 11/2011 | Allen, IV et al. | |
| 8,152,806 B2 | 4/2012 | Black et al. | |
| D661,394 S | 6/2012 | Romero et al. | |
| 8,679,140 B2 | 3/2014 | Butcher | |
| RE44,834 E | 4/2014 | Dumbauld et al. | |
| 8,939,973 B2 | 1/2015 | Garrison et al. | |
| 8,945,127 B2 | 2/2015 | Garrison et al. | |
| 9,113,907 B2 | 8/2015 | Allen, IV et al. | |
| 9,113,937 B2 | 8/2015 | Collings et al. | |
| 9,119,630 B2 | 9/2015 | Townsend et al. | |
| 9,124,013 B2 | 9/2015 | Frushhour et al. | |
| 2002/0099258 A1 * | 7/2002 | Staskin | A61B 17/0401 |
| | | | 600/29 |
| 2003/0018331 A1 | 1/2003 | Dycus et al. | |
| 2003/0109875 A1 | 6/2003 | Tetzlaff et al. | |
| 2003/0171747 A1 | 9/2003 | Kanehira et al. | |
| 2003/0229344 A1 | 12/2003 | Dycus et al. | |
| 2004/0176762 A1 | 9/2004 | Lawes et al. | |
| 2004/0243125 A1 | 12/2004 | Dycus et al. | |
| 2005/0154387 A1 | 7/2005 | Moses et al. | |
| 2007/0219409 A1 * | 9/2007 | Shimizu | A61B 1/00039 |
| | | | 600/112 |
| 2007/0260241 A1 | 11/2007 | Dalla Betta et al. | |
| 2008/0114349 A1 | 5/2008 | Treat | |
| 2008/0215048 A1 | 9/2008 | Hafner et al. | |
| 2010/0030205 A1 | 2/2010 | Herzon | |
| 2011/0184459 A1 | 7/2011 | Malkowski et al. | |
| 2011/0190765 A1 | 8/2011 | Chojin | |
| 2011/0251613 A1 | 10/2011 | Guerra et al. | |
| 2011/0301592 A1 | 12/2011 | Kerr et al. | |
| 2012/0083827 A1 * | 4/2012 | Artale | A61B 17/285 |
| | | | 606/207 |
| 2012/0136347 A1 | 5/2012 | Brustad et al. | |
| 2013/0018411 A1 | 1/2013 | Collings et al. | |
| 2013/0296843 A1 * | 11/2013 | Boudreaux | A61B 18/18 |
| | | | 606/33 |
| 2014/0031821 A1 | 1/2014 | Garrison | |
| 2014/0031860 A1 | 1/2014 | Stoddard et al. | |
| 2014/0046323 A1 | 2/2014 | Payne et al. | |
| 2014/0066910 A1 | 3/2014 | Nau, Jr. | |
| 2014/0066911 A1 | 3/2014 | Nau, Jr. | |
| 2014/0074085 A1 | 3/2014 | Kerr | |
| 2014/0074091 A1 | 3/2014 | Arya et al. | |
| 2014/0074092 A1 | 3/2014 | Horner et al. | |
| 2014/0094798 A1 | 4/2014 | Garrison et al. | |
| 2014/0094845 A1 | 4/2014 | Garrison et al. | |
| 2014/0100564 A1 | 4/2014 | Garrison | |
| 2014/0100568 A1 | 4/2014 | Garrison | |
| 2014/0100569 A1 | 4/2014 | Lawes et al. | |
| 2014/0100600 A1 | 4/2014 | Kendrick | |
| 2014/0104070 A1 | 4/2014 | Plaven | |

(56) References Cited

U.S. PATENT DOCUMENTS

| | | |
|---|---|---|
| 2014/0107443 A1 | 4/2014 | Hoarau et al. |
| 2014/0107646 A1 | 4/2014 | Garrison et al. |
| 2014/0107648 A1 | 4/2014 | Harper et al. |
| 2014/0107684 A1 | 4/2014 | Craig |
| 2014/0107685 A1 | 4/2014 | O'Neill et al. |
| 2014/0114309 A1 | 4/2014 | Payne et al. |
| 2014/0121507 A1 | 5/2014 | Nau, Jr. |
| 2014/0121508 A1 | 5/2014 | Latimer et al. |
| 2014/0121661 A1 | 5/2014 | Schmaltz et al. |
| 2014/0135758 A1 | 5/2014 | Mueller |
| 2014/0135763 A1 | 5/2014 | Kappus et al. |
| 2014/0148807 A1 | 5/2014 | Kendrick |
| 2014/0180281 A1 | 6/2014 | Rusin |
| 2014/0194875 A1 | 7/2014 | Reschke et al. |
| 2014/0221994 A1 | 8/2014 | Reschke |
| 2014/0221999 A1 | 8/2014 | Cunningham et al. |
| 2014/0230243 A1 | 8/2014 | Roy et al. |
| 2014/0243811 A1 | 8/2014 | Reschke et al. |
| 2014/0257284 A1 | 9/2014 | Artale |
| 2014/0257285 A1 | 9/2014 | Moua |
| 2014/0276803 A1 | 9/2014 | Hart |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| EP | 1645238 A1 | 4/2006 |
| EP | 1810625 A1 | 7/2007 |
| EP | 2347725 A1 | 7/2011 |
| EP | 2436330 A1 | 4/2012 |
| EP | 2659848 A2 | 11/2013 |
| EP | 2659849 A2 | 11/2013 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 11/1974 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/045589 | 6/2002 |
| WO | 2006021269 A1 | 3/2006 |
| WO | 05110264 A3 | 4/2006 |
| WO | 08/040483 A1 | 4/2008 |
| WO | 2011/018154 A1 | 2/2011 |
| WO | 2011/044343 A2 | 4/2011 |

OTHER PUBLICATIONS

U.S. Appl. No. 12/336,970, dated Dec. 17, 2008 (Sremcich et al.).
U.S. Appl. No. 13/731,674, dated Dec. 31, 2012 (Siebrecht et al.).
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery", 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.

(56) References Cited

OTHER PUBLICATIONS

Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room", 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex", 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
European Search Report from Application No. EP14158818.6 dated May 28, 2014.
The extended European Search Report from Application No. 14158819.4 dated Jun. 10, 2014.
Vallfors et al., "Automatically Controlled Bipolar Electrosoagulation-'COA-COMP'", Neurosurgical Review 7:2-3 (1984) pp. 187-190.
U.S. Appl. No. 08/926,869, dated Sep. 10, 1997 (Chandler et al.).
U.S. Appl. No. 09/177,950, dated Oct. 23, 1998 (Frazier et al.).
U.S. Appl. No. 09/387,883, dated Sep. 1, 1999 (Schmaltz et al.).

\* cited by examiner

VESSEL SEALING INSTRUMENT AND SWITCH ASSEMBLIES THEREOF

CROSS REFERENCE TO RELATED APPLICATION

The present application claims the benefit of and priority to U.S. Provisional Application Ser. No. 62/042,543, filed on Aug. 27, 2014, the entire contents of which are incorporated herein by reference.

BACKGROUND

1. Background of Related Art

The present disclosure relates to a forceps used for open or endoscopic surgical procedures. More particularly, the present disclosure relates to a switch assembly for a surgical forceps that can vary the resistance of an actuation switch of the surgical forceps.

2. Technical Field

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Certain surgical procedures require sealing and cutting blood vessels or vascular tissue. Several journal articles have disclosed methods for sealing small blood vessels using electrosurgery. An article entitled Studies on Coagulation and the Development of an Automatic Computerized Bipolar Coagulator, J. Neurosurg., Volume 75, July 1991, describes a bipolar coagulator which is used to seal small blood vessels. The article states that it is not possible to safely coagulate arteries with a diameter larger than 2 to 2.5 mm. A second article entitled Automatically Controlled Bipolar Electrocoagulation—"COA-COMP," Neurosurg. Rev. (1984), pp. 187-190, describes a method for terminating electrosurgical power to the vessel so that charring of the vessel walls can be avoided.

By utilizing an electrosurgical forceps, a surgeon can either cauterize, coagulate/desiccate, reduce or slow bleeding and/or seal vessels by controlling the intensity, frequency and duration of the electrosurgical energy applied to the tissue. Generally, the electrical configuration of electrosurgical forceps can be categorized in two classifications: 1) monopolar electrosurgical forceps; and 2) bipolar electrosurgical forceps.

Monopolar forceps utilize one active electrode associated with the clamping end effector and a remote patient return electrode or pad which is typically attached externally to the patient. When the electrosurgical energy is applied, the energy travels from the active electrode, to the surgical site, through the patient and to the return electrode.

Bipolar electrosurgical forceps utilize two generally opposing electrodes which are disposed on the inner opposing surfaces of the end effectors and which are both electrically coupled to an electrosurgical generator. Each electrode is charged to a different electric potential. Since tissue is a conductor of electrical energy, when the effectors are utilized to grasp tissue therebetween, the electrical energy can be selectively transferred through the tissue.

In order to effect a proper seal with larger vessels, two predominant mechanical parameters must be accurately controlled—the pressure applied to the vessel and the gap between the electrodes both of which affect thickness of the sealed vessel. More particularly, accurate application of the pressure is important to oppose the walls of the vessel, to reduce the tissue impedance to a low enough value that allows enough electrosurgical energy through the tissue, to overcome the forces of expansion during tissue heating and to contribute to the end tissue thickness which is an indication of a good seal. It has been determined that a fused vessel wall is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried and vessel sealing is defined as the process of liquefying the collagen in the tissue so that it reforms into a fused mass. Thus, coagulation of small vessels is sufficient to permanently close them. Larger vessels need to be sealed to assure permanent closure.

Numerous bipolar electrosurgical forceps have been proposed in the past for various open surgical procedures. However, some of these designs may not provide uniformly reproducible pressure to the blood vessel and may result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue.

Many of these instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created. Similarly, an amount of force required to actuate a switch of the forceps may be too high or too low depending on the preferences of the user of the forceps.

SUMMARY

According to one aspect of the present disclosure, a switch assembly for an electrosurgical instrument is provided. The switch assembly includes a switch housing, a switch, a first biasing member, and one or more additional biasing members. The switch is disposed within the switch housing and is movably disposed between an activated position to initiate delivery of electrosurgical energy and a deactivated position to terminate delivery of electrosurgical energy. The first biasing member is selectively positionable adjacent the switch and in communication therewith. The first biasing member includes a first thickness that provides a first resistance to resist movement of the switch between the activated and the deactivated positions when positioned in the switch housing. The additional biasing member is selectively interchangeable with the first biasing member. The additional biasing member(s) includes a different thickness than the first thickness to provide a different resistance than the first resistance and likewise resist movement of the switch between the activated and the deactivated positions when positioned in the switch housing.

In some embodiments, each biasing member includes a protrusion extending therefrom and the switch may include a protrusion extending therefrom. The protrusion of the biasing members and the protrusion of the switch engage one another during movement of the switch between the activated and deactivated positions.

In some embodiments, the biasing members have a U-shaped configuration. Each biasing member may include a first leg, a bent portion and a second leg. The first leg may be secured with the switch housing. The second leg may be coupled to the first leg via the bent portion. The second leg flexes inwardly towards the first leg upon movement of the switch from the deactivated position to the activated position.

In some embodiments, the switch assembly further includes a post extending from the switch and a snap dome in coaxial alignment with the post. Upon movement of the switch from the deactivated position to the activated position, the post engages the snap dome. The switch assembly may further include a spring disposed between the switch and the snap dome and configured to resiliently bias the switch toward the deactivated position.

In another aspect of the present disclosure, an electrosurgical instrument is provided. The electrosurgical instrument includes a first arm and a second arm movable relative to one another between an expanded position and an approximated position, a switch assembly, and a pair of jaw members. The switch assembly is disposed within the first arm and includes a switch housing, a switch, a first biasing member, and one or more additional biasing members. The switch is disposed within the switch housing and movably disposed between an activated position to initiate delivery of electrosurgical energy and a deactivated position to terminate delivery of electrosurgical energy. The first biasing member is selectively positionable adjacent the switch and in communication therewith. The first biasing member includes a first thickness that provides a first resistance to resist movement of the switch between the activated and the deactivated positions when positioned in the switch housing. The additional biasing member(s) is selectively interchangeable with the first biasing member. The additional biasing member(s) includes a different thickness than the first thickness to provide a different resistance than the first resistance and likewise resists movement of the switch between the activated and the deactivated positions when positioned in the switch housing. The first jaw member is coupled to the second arm and the second jaw member is coupled to the first arm. The jaw members are movable relative to one another between an expanded position and an approximated position.

In yet another aspect of the present disclosure, a method of performing an electrosurgical procedure is provided. The method includes providing a switch assembly of an electrosurgical instrument; selectively positioning one of a first and second biasing members adjacent a switch of the switch assembly and in communication therewith. In some embodiments, the method includes approximating first and second arms of the electrosurgical instrument to grasp tissue between first and second jaw members associated with the first and second arms; depressing the switch upon approximation of the first and second arms from a deactivated position to an intermediate position to relay information to the user corresponding to a grasping pressure applied to tissue grasped between the first and second jaw members; and depressing the switch to overcome one of a first resistance or a second, different resistance of the one of the first or additional biasing members such that the switch is disposed in an activated position to activate a source of electrosurgical energy to supply electrosurgical energy to the first and second jaw members.

In some embodiments, depressing the switch to overcome the first resistance or the different resistance of the respective biasing members includes passing a protrusion of the switch over a protrusion of the one of the first and additional biasing members.

In some embodiments, depressing the switch to overcome the first resistance or the different resistance of the respective biasing members includes flexing a second leg of the respective biasing member inwardly towards a first leg of the respective biasing members. It is contemplated that depressing the switch to overcome the first resistance or the different resistance of the respective biasing members may further include engaging a snap dome with a post extending from the switch.

In some embodiments, the method further includes removing the one of the first and additional biasing members from the switch housing; and positioning the other of the one of the first and additional biasing members adjacent the switch and in communication therewith.

In the drawings and in the description that follows, the term "proximal", as is traditional, will refer to the end of electrosurgical instrument that is closer to the user, while the term "distal" will refer to the end that is further from the user.

BRIEF DESCRIPTION OF THE DRAWINGS

Embodiments of the present disclosure are described herein with reference to the accompanying drawings, wherein.

DETAILED DESCRIPTION

Figure 1:
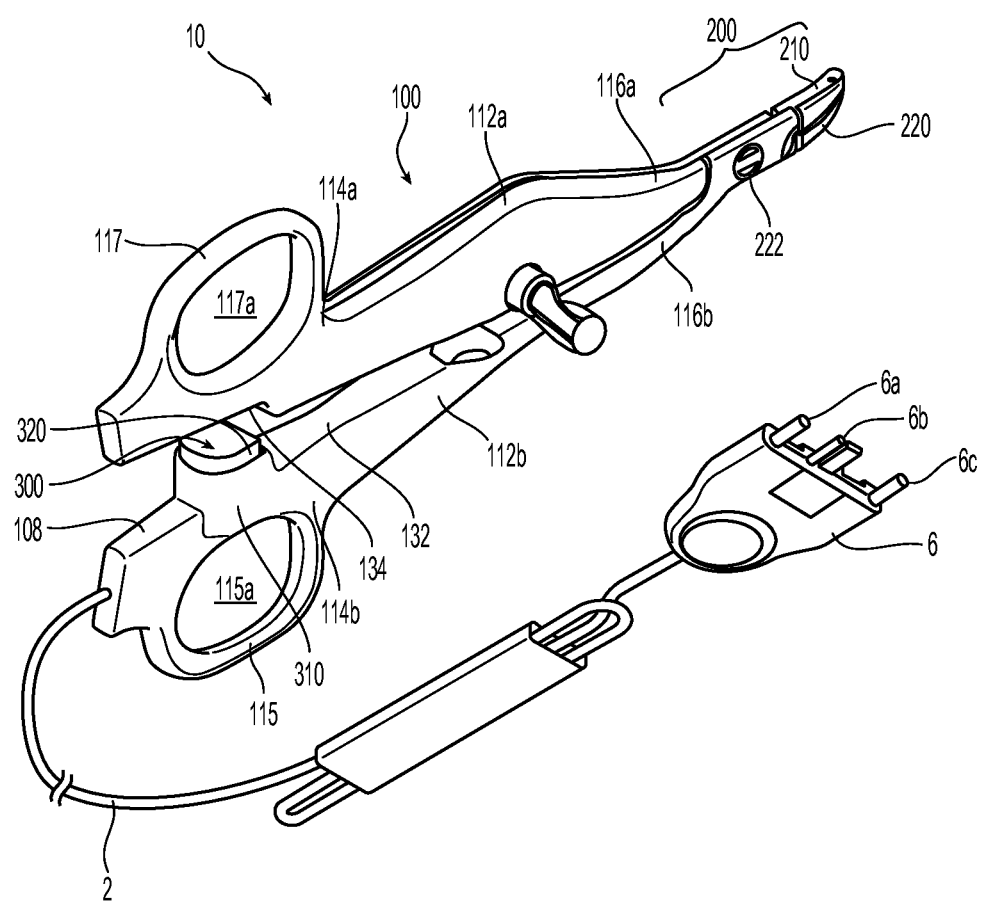
FIG. 1 is a right, perspective view of a forceps according to one embodiment of the present disclosure.
Figure 2:
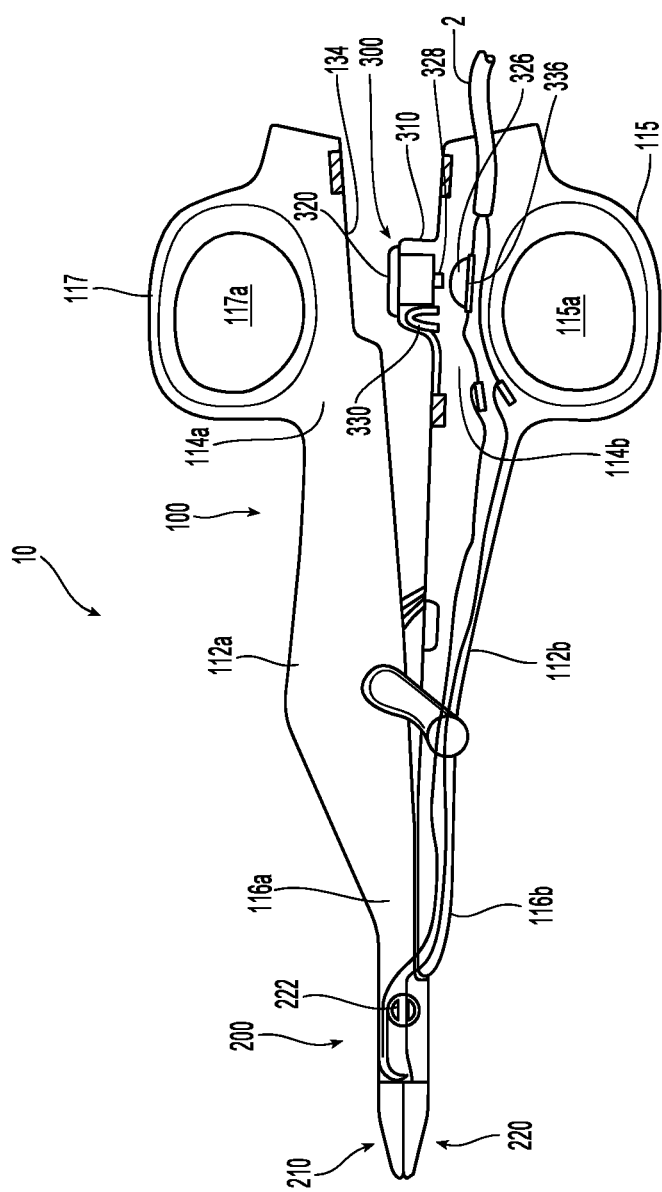
FIG. 2 is a side view of the forceps of FIG. 1, in part phantom, to show the inside of a switch assembly.

Referring initially to FIGS. 1 and 2, an electrosurgical instrument, such as, for example, a forceps 10 for use with open surgical procedures is provided. The forceps 10 may be configured for insertion through a trocar cannula (not shown) or access opening in a patient for endoscopic or laparoscopic procedures. Forceps 10 includes a handle assembly 100, an end effector 200 coupled to handle assembly 100 and actuatable by handle assembly 100, and a switch assembly 300 configured to control the transfer of electrosurgical energy to end effector 200. Switch assembly 300 has a plurality of biasing members selectively positionable therein to vary the resistance and/or tactile response to actuation of the handle assembly 100, as discussed in greater detail herein.

As shown in FIG. 1, an electrosurgical cable 2 having a plug 6 at its proximal end connects forceps 10 to an electrosurgical source or electrosurgical generator (not shown). A distal end of cable 2 is securely held to a shaft 112b of handle assembly 100 by a proximal shaft connector 108 and the proximal end of cable 2 includes plug 6 having prongs 6a, 6b, 6c that are configured to electrically and mechanically engage the electrosurgical generator. The electrosurgical generator is configured to supply electrosurgical energy to a pair of jaw members 210, 220 of the end effector 200 upon actuation of switch assembly 300 to effect treating (e.g., sealing) of tissue disposed between the jaw members 210, 220.

Handle assembly 100 includes a first arm or elongated shaft portion 112a and a second arm or elongated shaft portion 112b each having a proximal end 114a, 114b and a distal end 116a and 116b, respectively. End effector 200 attaches to distal ends 116a and 116b of shaft portions 112a and 112b, respectively. Opposing jaw members 210 and 220 are pivotably connected and movable relative to one another about a pivot 222 to grasp tissue therebetween.

Shaft portions 112a, 112b include respective handles 115, 117 disposed at proximal ends 114a and 114b thereof. Handles 115, 117 define respective finger holes 115a, 117a therethrough for receiving a finger of the user. Handles 115 and 117 facilitate movement of shaft portions 112a and 112b relative to one another, which, in turn, pivot jaw members 210 and 220 from an open or expanded position, in which jaw members 210 and 220 are disposed in spaced relation to one another, to a clamping or approximated position, in which jaw members 210 and 220 cooperate to grasp tissue therebetween.

Figure 3A:
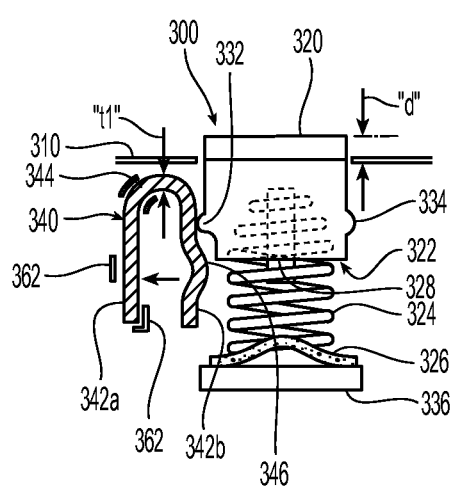
FIG. 3A is a plan view, in part phantom, of the switch assembly shown in FIG. 2 including a first biasing member selectively positioned therein.
Figure 3B:
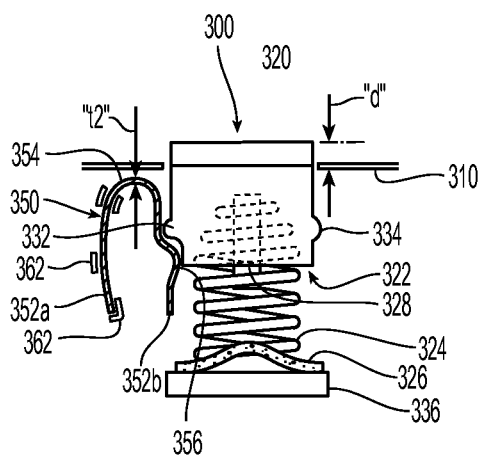
FIG. 3B is a plan view, in part phantom, of the switch assembly shown in FIG. 2 including a second biasing member selectively positioned therein.

With reference to FIGS. 1, 2, 3A, and 3B, switch assembly 300 includes a switch housing 310, a switch 320, a first, removable biasing member 340 (FIG. 3A), and one or more second or additional, removable biasing members, e.g., biasing member 350 (FIG. 3B). Switch assembly 300 is disposed with proximal end 114b of shaft portion 112b and coplanar with proximal end 114a of shaft portion 112a such that switch assembly 300 is actuatable by proximal end 114a of shaft portion 112a during approximation of proximal ends 114a, 114b of shaft portions 112a, 112b.

Switch housing 310 extends from an inner facing surface 132 of shaft portion 112b and is configured to house switch 320 (and the electrical components associated therewith), which may be in the form of a depressible button. In some embodiments, switch housing 310 may be integrally connected to or monolithically formed with proximal end 114b of shaft portion 112b or proximal end 114a of shaft portion 112a.

Switch 320 is movably disposed within switch housing 310 between an activated position to initiate delivery of electrosurgical energy to jaw members 210, 220 and a deactivated position to terminate delivery of electrosurgical energy to jaw members 210, 220. Switch 320 aligns with an opposing inner facing surface 134 of proximal end 114a of shaft portion 112a such that upon approximation of shaft portions 112a and 112b, switch 320 is depressed into biasing engagement with opposing inner facing surface 134 of proximal end 114a of shaft portion 112a.

With reference to FIGS. 3A and 3B, switch 320 protrudes a distance "d" from switch housing 310 such that switch 320 can be axially translated distance "d" upon engagement of proximal end 114a of shaft portion 112a therewith. Switch 320 has a cylindrical shape and defines a cavity 322 therein. A spring, such as, for example, a coil spring 324 is disposed in cavity 322 captured between switch 320 and a dome switch 326, as described in greater detail below. Coil spring 324 is configured to resiliently bias switch 320 toward the deactivated position. Switch 320 further includes a post 328 disposed within cavity 322 and extending through a hollow core of coil spring 324. Switch 320 includes a first protrusion 332 extending from a first radial side thereof and configured for engagement with first or second biasing members 340, 350. Switch 320 may also include a second protrusion 334 extending from a second radial side thereof also configured for engagement with first or second biasing members 340, 350.

As mentioned above, switch assembly 300 includes snap dome or dome switch 326 and a printed circuit board 336 that supports dome switch 326. Dome switch 326 is in coaxial alignment with post 324 of switch 320 such that post 324 engages dome switch 326 upon movement of switch 320 from the deactivated position to the activated position. Printed circuit board 336 is attached to switch housing 310 and electrically couples the electrosurgical source or generator (not shown) and jaw members 210, 220 such that upon inversion of dome switch 326, via engagement with post 324, an electrical pathway is created through which electrosurgical energy can travel from the electrosurgical source to jaw members 210, 220.

With continued reference to FIGS. 3A and 3B, first biasing member 340 (FIG. 3A) and second biasing member 350 (FIG. 3B) are selectively positionable adjacent switch 320 and in communication therewith, as described in greater detail below. First biasing member 340 includes a first thickness "t1" that provides a first resistance to compression thereof to resist movement of switch 320 between the activated and deactivated positions when first biasing member 340 is positioned in switch housing 310. Second biasing member 350 includes a second thickness "t2," less than thickness "t1" of first biasing member 340. Second thickness "t2" of second biasing member 350 provides a second resistance to compression thereof that is less than the first resistance provided by first thickness of "t1" of first biasing member 340. The second resistance of second biasing member 350 resists movement of switch 320 between the activated and deactivated positions when second biasing member 350 is positioned in switch housing 310. It is contemplated that a plurality of biasing members of varying thicknesses or varying material properties and, in turn, varying resistances, may be provided that are each selectively positionable adjacent switch 320 and in communication therewith. This allows a manufacturer or surgeon, during assembly of forceps 10, to selectively adjust the force required to actuate switch 320.

First and second biasing members 340, 350 each have a U-shaped configuration and are fabricated from plastic. In some embodiments, first and second biasing members 340, 350 may be variously configured, such as, for example, tapered, uniform, non-uniform, circular, triangular, squared, arcuate, undulating and/or polygonal and may be fabricated from any suitable, flexible material. First and second biasing members 340, 350 each include a first leg 342a, 352a, an intermediate bent portion 344, 354, and a second leg 342b, 352b. In some embodiments, first leg 342a of first biasing member 340 may have the same thickness as first leg 352a of second biasing member 350 while bent portions 344, 354 of biasing members 340, 350 have different thicknesses from one another.

First legs 342a, 352a are configured to be selectively secured within switch housing 310 via a plurality of capture members 362 extending from switch housing 310. Capture members 362 are arranged to define a channel configured to accommodate first legs 342a, 352a therein. It is envisioned that first legs 342a, 352a may be configured for snap fit engagement with capture members 362 such that first legs 342a, 352a are prevented from moving relative to switch housing 310.

Second legs 342b, 352b are coupled to first legs 342a, 352a, respectively, via bent portions 344, 354 such that first legs 342a, 352a and second legs 342b, 352b are in substantial side-by-side, parallel alignment with one another. In some embodiments, first and second legs 342a, 352a, 342b, 352b may be variously oriented relative to one another, such as, for example, positioned at an acute angle, an obtuse angle, or a substantially perpendicular angle relative to one another. Second legs 342b, 352b each have a protrusion or an arcuate bump 346, 356 extending from an intermediate portion thereof. When one of first or second biasing members 340, 350 is selectively positioned in switch housing 310, bump 346 or bump 356 of second legs 342b, 352b, respectively, is in coaxial alignment with protrusion 332 of switch 320. During movement of switch 320 between the activated and deactivated positions, protrusion 332 and bump 346 of first biasing member 340 or bump 356 of second biasing member 350 engage and pass over one another. Upon bump 346 and protrusion 332 or bump 356 and protrusion 332 passing over one another, second legs 342b, 352b of first or second biasing members 340, 350, respectively, flex inwardly towards respective first legs 342a, 352a under a resistance.

In some embodiments, the resistance of biasing members 340, 350 may be adjusted by varying the size and/or shape of bumps 346, 356. For example, a larger bump 346, 356 will correspond to a greater resistance of biasing members 340, 350, respectively.

In operation, one of the first or second biasing members 340, 350 is selectively positioned adjacent switch 320 and in communication therewith. For example, first biasing member 340 may be selected because its ability to resist movement of switch 320 between the activated and deactivated positions provides for a preferred tactility to a user of forceps 10. Alternately, a user that prefers switch 320 to be more responsive to a force exerted thereon may prefer to use a forceps 10 having second biasing member 350 selectively positioned within switch housing 310. In some embodiments, a plurality of biasing members may be provided to accommodate various user preferences.

Figure 4A:
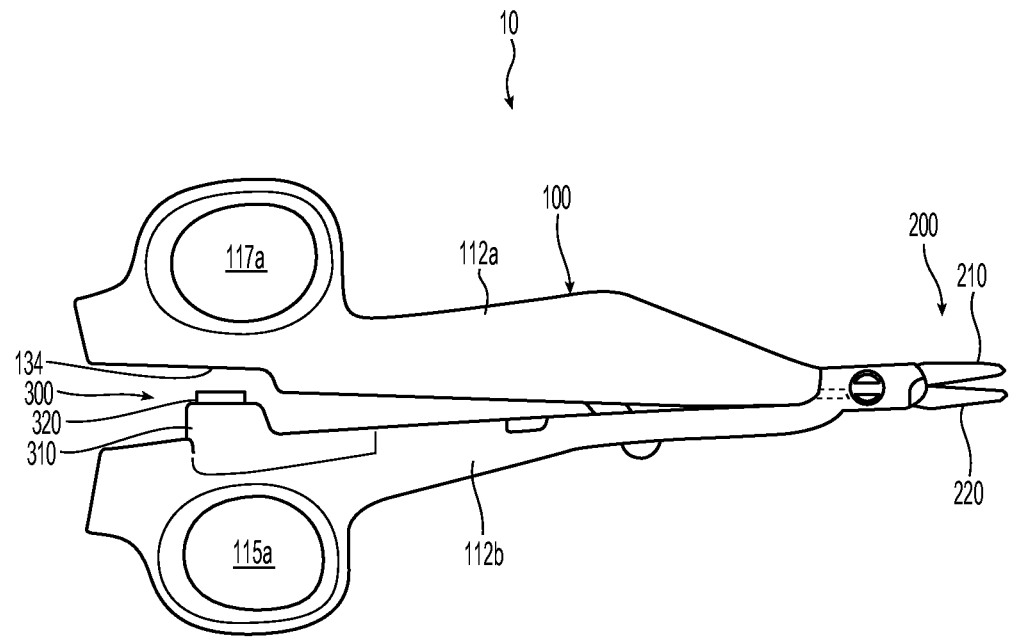
FIGS. 4A and 4B are side views of the forceps of FIG. 1 illustrating actuation thereof between open and approximated positions.
Figure 4B:
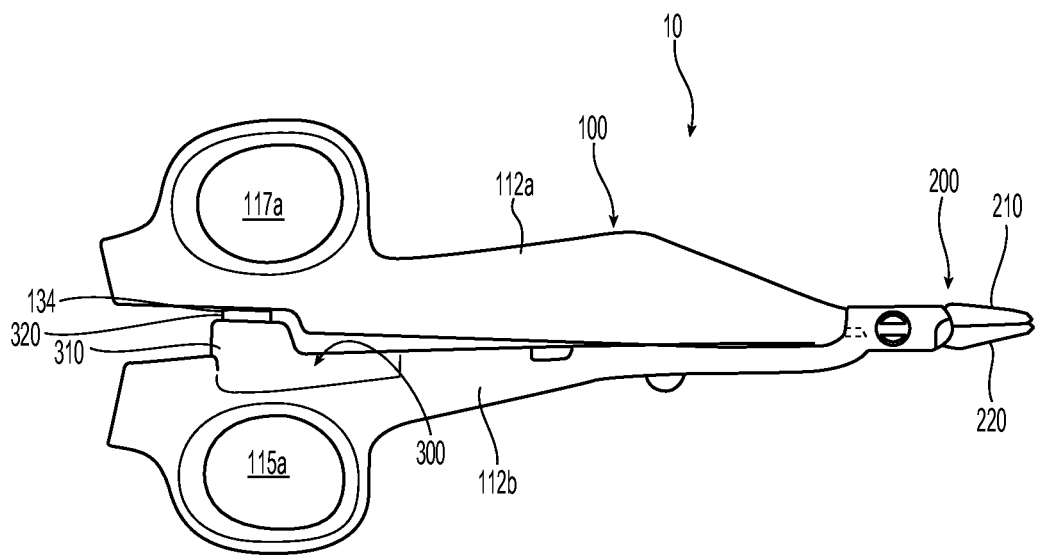

With one of first or second biasing members 340, 350 disposed within switch housing 310, first and second shaft portions 112a, 112b may be approximated and, in turn, jaw members 210, 220 are pivoted to an approximated position to grasp tissue therebetween. Upon approximating first and second shaft portions 112a, 112b, inner facing surface 134 of shaft portion 112a engages switch 320 to depress switch 320 from the deactivated position, as shown in FIG. 4A, to an intermediate position, as shown in FIG. 4B, to relay information (i.e., a first tactile response) to the user corresponding to a predetermined grasping pressure applied to the tissue grasped between first and second jaw members 210, 220. The first tactile response indicates to the user that the maximum grasping pressure has been reached before end effector 200 is energized where the user is free to approximate, manipulate, and grasp tissue as needed.

Continued approximation of first and second jaw members 210, 220 overcomes the first resistance provided by first biasing member 340 (or the second resistance provided by second biasing member 350) to further depress switch 320 to the activated position (not shown). To overcome the resilient bias of first or second biasing members 340, 350, a sufficient amount of force is required to pass protrusion 332 of switch 320 over bump 346 of first biasing member 340 or bump 356 of second biasing member 350. Upon overcoming the resistance provided by first or second biasing members 340, 350, post 328 of switch 320 engages snap dome 326 to dispose switch 320 in the activated position. In the activated position, a source of electrosurgical energy is activated to supply electrosurgical energy to first and second jaw members 210, 220 to seal the tissue disposed therebetween. Upon switch 320 moving to the activated position, the user receives a second tactile response indicating the electrosurgical activation of end effector 200.

In some embodiments, switch 320 may include a plurality of other tactile responses between the above discussed first and second tactile responses and/or subsequent to the second tactile response that correspond to particular functions of forceps 10 such as, for example, operation of a knife (not shown) and/or an actuation assembly (not shown), and/or operation of a safety lockout mechanism (not shown) associated with the actuation assembly (not shown), as discussed in detail in U.S. application Ser. No. 14/105,374, which is incorporated by reference herein.

The various embodiments disclosed herein may also be configured to work with robotic surgical systems and what is commonly referred to as "Telesurgery." Such systems employ various robotic elements to assist the surgeon in the operating theatre and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A switch assembly for an electrosurgical instrument, comprising:
   a switch housing;
   a switch disposed within the switch housing and movably disposed between an activated position to initiate delivery of electrosurgical energy and a deactivated position to terminate delivery of electrosurgical energy;

a first biasing member selectively positionable adjacent the switch and in communication therewith, wherein the first biasing member includes a first thickness that provides a first resistance to resist movement of the switch between the activated and the deactivated positions when positioned in the switch housing, the switch having a portion that engages and slides along and relative to a portion of the first biasing member during movement of the switch between the activated and deactivated positions, wherein when the switch moves toward the activated position, the portion of the switch moves toward the portion of the biasing member on an axis that intersects both the portion of the switch and the portion of the biasing member, wherein the switch moves to the activated position to initiate delivery of the electrosurgical energy after the portion of the switch slides past the portion of the first biasing member.

2. The switch assembly according to claim 1, wherein the portion of the first biasing member is a protrusion extending therefrom and the portion of the switch is a protrusion extending therefrom that directly slidingly contacts the protrusion of the first biasing member during movement between the activated and deactivated positions.

3. The switch assembly according to claim 2, wherein the protrusion of the switch and the protrusion of the first biasing member overlap one another when the switch is between the activated and deactivated positions.

4. The switch assembly according to claim 1, wherein the first biasing member has a U-shaped configuration.

5. The switch assembly according to claim 4, wherein the first biasing member includes:
a first leg secured with the switch housing;
a bent portion; and
a second leg coupled to the first leg via the bent portion, wherein the second leg flexes inwardly towards the first leg and out of a path of the portion of the switch upon sliding movement of the portion of the switch over and relative to the portion of the first biasing member.

6. The switch assembly according to claim 5, wherein the portion of the switch is a protrusion extending therefrom, and the portion of the first biasing member is a protrusion extending from the second leg thereof toward the protrusion of the switch.

7. The switch assembly according to claim 1, further comprising:
a post extending from the switch; and
a snap dome in coaxial alignment with the post such that upon movement of the switch from the deactivated position to the activated position the post engages the snap dome.

8. The switch assembly according to claim 7, further comprising a spring disposed between the switch and the snap dome and configured to resiliently bias the switch toward the deactivated position.

9. The switch assembly according to claim 1, further comprising at least one additional biasing member selectively interchangeable with the first biasing member, wherein the at least one additional biasing member includes a different thickness than the first thickness that provides a different resistance than the first resistance to resist movement of the switch between the activated and the deactivated positions when positioned in the switch housing.

10. The switch assembly according to claim 1, wherein the switch and the first biasing member are in direct sliding contact with one another.

11. An electrosurgical instrument, comprising:
a first arm and a second arm movable relative to one another between an expanded position and an approximated position;
a switch assembly disposed within the first arm and including:
a switch housing;
a switch disposed within the switch housing and movably disposed between an activated position to initiate delivery of electrosurgical energy and a deactivated position to terminate delivery of electrosurgical energy;
a first biasing member selectively positionable adjacent the switch and in communication therewith, wherein the first biasing member includes a first thickness that provides a first resistance to resist movement of the switch between the activated and the deactivated positions when positioned in the switch housing, the switch having a portion that engages and slides along and relative to a portion of the first biasing member during movement of the switch between the activated and deactivated positions, wherein when the switch moves toward the activated position, the portion of the switch moves toward the portion of the biasing member on an axis that intersects both the portion of the switch and the portion of the biasing member, wherein the switch moves to the activated position to initiate delivery of the electrosurgical energy after the portion of the switch slides past the portion of the first biasing member; and
a first jaw member coupled to the second arm and a second jaw member coupled to the first arm, the jaw members movable relative to one another between an expanded position and an approximated position, wherein the portion of the switch moving into contact with the portion of the biasing member during movement of the switch toward the activated position corresponds with a maximum grasping pressure of the first and second members before the delivery of the electrosurgical energy.

12. The electrosurgical instrument according to claim 11, wherein the portion of the first biasing member is a protrusion extending therefrom and the portion of the switch is a protrusion extending therefrom that releasably contacts the protrusion of the first biasing member.

13. The electrosurgical instrument according to claim 12, wherein the protrusion of the switch and the protrusion of the first biasing member overlap one another when the switch is between the activated and deactivated positions.

14. The electrosurgical instrument according to claim 11, wherein the first biasing member has a U-shaped configuration.

15. The electrosurgical instrument according to claim 14, wherein the first biasing member includes:
a first leg secured with the switch housing;
a bent portion; and
a second leg coupled to the first leg via the bent portion, wherein the second leg flexes inwardly towards the first leg and out of a path of the portion of the switch upon sliding movement of the portion of the switch over and relative to the portion of the first biasing member.

16. The electrosurgical instrument according to claim 15, wherein the portion of the switch is a protrusion extending therefrom, and the portion of the first biasing member is a protrusion extending from the second leg thereof toward the protrusion of the switch.

17. The electrosurgical instrument according to claim 11, wherein the switch assembly further includes:
- a post extending from the switch; and
- a snap dome in coaxial alignment with the post such that upon movement of the switch from the deactivated position to the activated position the post engages the snap dome.

18. The electrosurgical instrument according to claim 17, wherein the switch assembly further includes a spring disposed between the switch and the snap dome and configured to resiliently bias the switch toward the deactivated position.

19. The electrosurgical instrument according to claim 11, further comprising at least one additional biasing member selectively interchangeable with the first biasing member, wherein the at least one additional biasing member includes a different thickness than the first thickness that provides a different resistance than the first resistance to resist movement of the switch between the activated and the deactivated positions when positioned in the switch housing.

20. The electrosurgical instrument according to claim 11, wherein the switch and the first biasing member are in sliding contact with one another.

* * * * *